United States Patent
Thomas

(10) Patent No.: US 11,517,563 B2
(45) Date of Patent: Dec. 6, 2022

(54) LIQUID NIMODIPINE COMPOSITIONS

(71) Applicant: Arbor Pharmaceuticals, LLC, Atlanta, GA (US)

(72) Inventor: Hugh Greg Thomas, Carrollton, GA (US)

(73) Assignee: Azurity Pharmaceuticals, Inc., Woburn, MA (US)

( * ) Notice: Subject to any disclaimer, the term of this patent is extended or adjusted under 35 U.S.C. 154(b) by 0 days.

(21) Appl. No.: 17/708,669

(22) Filed: Mar. 30, 2022

(65) Prior Publication Data

US 2022/0218684 A1    Jul. 14, 2022

Related U.S. Application Data

(63) Continuation-in-part of application No. 17/530,728, filed on Nov. 19, 2021, which is a continuation of application No. 16/722,513, filed on Dec. 20, 2019, now Pat. No. 11,207,306, which is a continuation of application No. 16/407,980, filed on May 9, 2019, now Pat. No. 10,576,070, which is a continuation of application No. 15/954,357, filed on Apr. 16, 2018, now Pat. No. 10,342,787.

(60) Provisional application No. 62/621,953, filed on Jan. 25, 2018.

(51) Int. Cl.
*A61K 31/4422*   (2006.01)
*A61K 47/10*     (2017.01)
*A61K 9/08*      (2006.01)
*A61P 25/00*     (2006.01)

(52) U.S. Cl.
CPC .......... *A61K 31/4422* (2013.01); *A61K 9/08* (2013.01); *A61K 47/10* (2013.01); *A61P 25/00* (2018.01)

(58) Field of Classification Search
CPC .. A61K 31/485; A61K 9/0019; A61K 9/1617; A61K 9/1635; A61K 9/1647; A61K 31/4422; A61K 47/10; A61K 9/08; A61P 25/00
See application file for complete search history.

(56) References Cited

U.S. PATENT DOCUMENTS 8,486,374 B2   7/2013   Tamarkin
9,339,553 B2   5/2016   Zhang

FOREIGN PATENT DOCUMENTS

CN          101129366        2/2008
WO     WO-2007047406 A2 *   4/2007   ......... A61K 31/4422

OTHER PUBLICATIONS

Barmpalexis et al. J of Pharmaceutical and Biomedical Analysis, 49, 2009, 1192-1202.
Nymalize https://www.accessdata.fda.gov/drugsatfdadocs/label/2013/203340lbl.pdf, FDA, 2013.
Hai et al. CN 101129366, English translation, Feb. 27, 2008.
CN 101129366, English translation, Feb. 27, 2008.

* cited by examiner

*Primary Examiner* — Umamaheswari Ramachandran
(74) *Attorney, Agent, or Firm* — King & Spalding

(57) ABSTRACT

Liquid compositions comprising nimodipine having improved nimodipine concentrations are provided herein. Methods of improving neurological outcome by reducing the incidence and severity of ischemic deficits in patients with subarachnoid hemorrhage from ruptured intracranial berry aneurysms with the liquid compositions of the present invention are also detailed herein.

5 Claims, No Drawings

LIQUID NIMODIPINE COMPOSITIONS

CROSS REFERENCE TO RELATED APPLICATIONS

This application is a continuation-in-part of U.S. patent application Ser. No. 17/530,728, filed Nov. 19, 2021; which is a continuation of U.S. patent application Ser. No. 16/722,513, filed Dec. 20, 2019, now U.S. Pat. No. 11,207,306; which is a continuation of U.S. patent application Ser. No. 16/407,980, filed May 9, 2019, now U.S. Pat. No. 10,576,070; which is a continuation of U.S. patent application Ser. No. 15/954,357, filed Apr. 16, 2018, now U.S. Pat. No. 10,342,787; which claims the benefit of U.S. Provisional Application No. 62/621,953, filed Jan. 25, 2018, the contents of which are incorporated by reference in their entirety.

FIELD OF THE INVENTION

The present invention relates generally to liquid nimodipine compositions with improved stability compared to existing aqueous compositions comprising nimodipine. The present invention also generally relates to methods of treating conditions for which nimodipine is indicated comprising administering the liquid nimodipine composition to a patient in need thereof.

BACKGROUND OF THE INVENTION

Nimodipine is a dihydropyridine derivative calcium channel blocker indicated for the improvement of neurological outcome by reducing the incidence and severity of ischemic deficits in patients with subarachnoid hemorrhage (SAH) from ruptured intracranial berry aneurysms regardless of their post-ictus neurological condition (i.e., Hunt and Hess Grades I-V). Nimodipine has the chemical name 1,4-dihydro-2,6-dimethyl-4-(m-nitrophenyl)-3,5-pyridinedicarboxylate and the structure shown below:

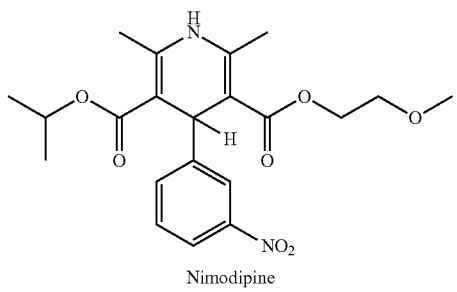

Nimodipine

NIMOTOP® (Bayer Pharmaceuticals Corp.) is a liquid-filled capsule formulation of nimodipine for oral dosing. Each NIMOTOP® capsule contains 30 mg of nimodipine and is commonly administered in a two-capsule 60 mg dose.

The prescribing information for NIMOTOP® states that, if the capsule cannot be swallowed (e.g., at the time of surgery) or if the patient is unconscious, a hole should be made in both ends of the capsule with an 18 gauge needle, and the contents of the capsule extracted into a syringe. To help minimize administration errors, it is recommended that the syringe be labeled "Not for IV Use". The contents should then be emptied into the patient's in situ naso-gastric tube and washed down the tube with 30 mL of normal saline (0.9%).

In addition to this method of delivery being cumbersome and time consuming, it is also dependent on the ability of the particular practitioner. It is possible that the practitioner extracts less than the full amount of the liquid dose from the capsule, leading to under dosing and insufficient treatment.

NYMALIZE® (Arbor Pharmaceuticals, LLC) was the first marketed oral nimodipine solution, eliminating the need for needle extraction of nimodipine from capsules for patients that cannot consume capsules. NYMALIZE® is supplied in bottles that should be stored between 20° C. to 25° C. (68° F. to 77° F.), protected from light, and unrefrigerated. The recommended dose is 20 mL (containing 60 mg of nimodipine) every 4 hours for 21 consecutive days. The inactive ingredients in NYMALIZE® are ethanol, glycerin, methylparaben, polyethylene glycol, sodium phosphate monobasic and water (about 20% by volume).

It has been found that NYMALIZE® slowly degrades under certain conditions (e.g., elevated temperature and humidity). One of the degradants includes nimodipine related compound A, (2-Methoxyethyl 1-methylethyl 2,6-dimethyl-4-(3-nitrophenyl)pyridine-3,5-dicarboxylate) having the following structure:

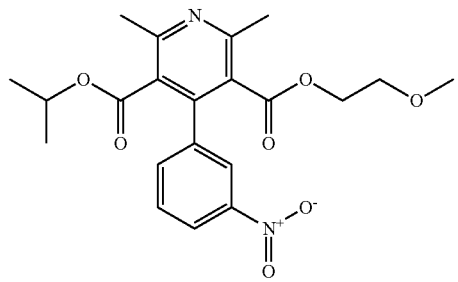

Accordingly, there remains a need for liquid nimodipine formulations with improved stability and decreased degradation.

SUMMARY OF THE INVENTION

In one aspect, the present invention generally relates to novel liquid pharmaceutical compositions containing nimodipine that have improved shelf-life and decreased nimodipine-related degradation compared to existing liquid pharmaceutical compositions.

In another aspect, the present invention relates to novel liquid compositions comprising nimodipine in concentrations higher than those of other liquid compositions, e.g., NYMALIZE®. The concentration of nimodipine in NYMALIZE® (60 mg/20 mL) is 3 mg/mL. The liquid composition of the present invention allows use of a higher nimodipine concentrations per dose, thereby lowering a patient's daily intake of the liquid composition compared to NYMALIZE®.

In preferred embodiments, the liquid compositions of the present invention have a nimodipine concentration of about 6 mg/mL or greater.

In one aspect, the present invention provides a liquid composition comprising nimodipine. In one embodiment, the liquid composition comprises nimodipine and a solvent comprising ethanol, wherein the ethanol is present in the composition in an amount of about 1% or less by weight.

In still another embodiment, the present invention provides a liquid composition comprising nimodipine, wherein about 5% or less nimodipine degradation is observed over a period of at least three months when exposed to 40° C. and 75% relative humidity.

In certain embodiments, the present invention provides a liquid composition comprising nimodipine, wherein about 4.5% or less nimodipine degradation is observed over a period of at least three months when exposed to 40° C. and 75% relative humidity.

In another embodiment, the present invention provides a liquid composition comprising nimodipine and about 1.2% or less nimodipine related compound A when the composition is exposed to 40° C. and 75% relative humidity over a period of at least three months.

In a particular embodiment, the present invention provides a liquid composition comprising nimodipine and about 0.01% to about 1.2% nimodipine related compound A when the composition is exposed to 40° C. and 75% relative humidity over a period of at least three months, and more particularly, about 0.10% to about 0.8% nimodipine related compound A.

In one embodiment, the present invention provides a liquid composition comprising nimodipine and at least about 90% less nimodipine related compound A than NYMALIZE® when both compositions area exposed to 40° C. and 75% relative humidity over a period of at least three months, and more particularly, at least about 75% less, at least about 60% less or at least about 50% less nimodipine related compound A than NYMALIZE®.

In one embodiment, the present invention provides a liquid composition comprising nimodipine and substantially no nimodipine related compound A. In one embodiment, the present invention provides a liquid composition comprising nimodipine, wherein about 2.0% or less total impurities are observed over a period of at least three months when exposed to 40° C. and 75% relative humidity.

In another embodiment, the present invention provides a liquid composition comprising nimodipine, wherein about 1.0% or less total impurities are observed over a period of at least three months when exposed to 40° C. and 75% relative humidity.

In a particular embodiment, the present invention provides a liquid composition comprising nimodipine, wherein about 0.01% to about 2.0% total impurities are observed over a period of at least three months when exposed to 40° C. and 75% relative humidity, and more particularly, about 0.1% and about 1.9% total impurities.

In one embodiment, the present invention provides a liquid composition comprising nimodipine and at least about 90% less total impurities than NYMALIZE® when both compositions are exposed to 40° C. and 75% relative humidity over a period of at least three months, and more particularly, at least about 75% less, at least about 60% less or at least about 50% less total impurities than NYMALIZE®.

In one embodiment, the present invention provides a liquid composition comprising nimodipine and substantially no total impurities are observed over a period of at least three months when exposed to 40° C. and 75% relative humidity.

In another embodiment, the present invention provides a liquid composition comprising nimodipine and about 0.3% or less nimodipine related compound A over a period of at least three months when exposed to 25° C. and 60% relative humidity.

In another embodiment, the present invention provides a liquid composition comprising nimodipine and about 0.01% to about 0.3% nimodipine related compound A over a period of at least three months when exposed to 25° C. and 60% relative humidity, or more particularly, about 0.01% and about 0.1% nimodipine related compound A.

In one embodiment, the present invention provides a liquid composition comprising nimodipine and at least about 90% less nimodipine related compound A than NYMALIZE® when both compositions are exposed to 25° C. and 60% relative humidity over a period of at least three months, and more particularly, at least about 85% less, at least about 69% less 75% less, at least about 60% less or at least about 50% less nimodipine related compound A than NYMALIZE®.

In a particular embodiment, the liquid composition comprises nimodipine and substantially no nimodipine related compound A when the composition is exposed to 25° C. and 60% relative humidity over a period of at least three months.

In another embodiment, the present invention provides a liquid composition comprising nimodipine, wherein about 0.4% or less total impurities are observed over a period of at least three months when exposed to 25° C. and 60% relative humidity. In a particular embodiment, the present invention provides a liquid composition comprising nimodipine, wherein about 0.01% to about 0.4% total impurities are observed over a period of at least three months when exposed to 25° C. and 60% relative humidity, and more particularly, about 0.1% and about 0.4% total impurities.

In one embodiment, the present invention provides a liquid composition comprising nimodipine and at least about 90% less total impurities related than NYMALIZE® when both compositions are exposed to 25° C. and 75% relative humidity over a period of at least three months, and more particularly, at least about 85% less, at least about 60% less 75% less, at least about 60% less or at least about 50% less total impurities than NYMALIZE®.

In one embodiment, the present invention provides a liquid composition comprising nimodipine and substantially no total impurities are observed over a period of at least three months when exposed to 25° C. and 60% relative humidity.

In another aspect, the present invention provides a method of treating disorders, or symptoms associated with disorders for which nimodipine provides a therapeutic effect.

In one embodiment, the present invention provides a method of reducing the incidence and severity of ischemic deficits in patients with subarachnoid hemorrhage from ruptured intracranial berry aneurysms comprising administering to a patient in need thereof an effective amount of a liquid composition described herein.

DETAILED DESCRIPTION OF THE INVENTION

The present invention relates to liquid compositions comprising nimodipine. In some embodiments, the liquid compositions of the invention have improved stability and decreased degradants compared to existing liquid pharmaceutical compositions, e.g. NYMALIZE®. In other embodiments, the liquid compositions have increased nimodipine concentrations compared to existing liquid pharmaceutical compositions, e.g. NYMALIZE®. When comparisons are made, it is understood to be under the same or similar conditions.

I. Definitions

Pharmaceutical compositions and medicaments may be described as mixtures of two or more components "by volume," which is herein defined as the volume due to one component divided by the volume of all components of the pharmaceutical composition. This ratio may be converted to or reported as a percentage of the total composition volume. Such a quantity may also be indicated by "v/v" or "percent v/v." Similarly, the phrase "by weight" describes the weight due to one component divided by the weight of all components of the composition. This ratio may be converted to or reported as a percentage of the total composition weight. Such a quantity may also be indicated by "w/w" or "percent w/w."

As used herein, the term "degradation product" refers to impurities resulting from chemical changes that occur during drug manufacturing, storage and/or transportation in response to changes in light, temperature, pH, and humidity, or due to inherent characteristics of the active pharmaceutical substance, such as their reaction with excipients or on contact with the packaging. For example, the degradation products of nimodipine include: (1) 2-methoxyethyl 1-methylethyl-2,6-dimethyl4-(3-nitrophenyl) pyridine-3,5-dicarboxylate (i.e., nimodipine related compound A); (2) bis (1-methylethyl)-2,6-dimethyl-4-(3-nitrophenyl), 1,4-dihydro-pyridine-3,5-dicarboxylate and (3) bis (2-methoxyethyl)-2,6-dimethyl-4-(3-nitrophenyl)-1,4-dihydro pyridine-3,5-dicarboxylate.

As used herein, the term "dosage unit" or "unit dose" (used interchangeably) refers to one dose of the liquid composition of the present invention, as administered to the patient. For example, multiple dosage units can be present when the liquid composition of the present invention is stored in a bottle. A fraction of that bottle, i.e. a single dosage unit, is administered to the patient at a time. In the current NYMALIZE® formulation, a dosage unit is 20 mL (containing 60 mg of nimodipine).

As used herein, the term "effective amount" refers the amount of active agent present in the composition that is needed to provide a desired level of active agent in the bloodstream or the target tissue. The precise amount will depend upon numerous factors and can readily be determined by one skilled in the art, based upon the information provided herein and available in the relevant literature.

As used herein, the term "nimodipine" includes the racemate, other mixtures of (+)- and (−)-isomers, and single enantiomers, but may be specifically set forth as the racemate, (+)-isomer, (−)-isomer, or any mixture of both (+)- and (−)-isomers. As used herein, the term "patient" refers to a living organism suffering from or prone to a condition that can be prevented or treated by administration of a composition described herein, and includes both humans and animals. In one embodiment, the patient is a human patient.

As used herein, the terms "pharmaceutically acceptable excipient" or "pharmaceutically acceptable carrier" refers to an excipient that can be included in the compositions of the invention and that causes no significant adverse toxicological effects to the patient to which the composition is administered.

As used herein, the term "stable" or "stabilized" with respect to a composition is one in which the active ingredient retains its chemical stability, physical stability, microbiological stability, therapeutic stability and/or toxicological stability. Stability may be measured under a variety of conditions including long-term stability, intermediate stability, accelerated stability, real-time stability or a combination thereof. In real-time stability testing, a product is stored at recommended storage conditions and monitored until it fails the specification. In accelerated stability tests, a product is stored at elevated stress conditions (such as temperature, humidity, and pH). Degradation at the recommended storage conditions can be predicted using known relationships between the acceleration factor and the degradation rate.

As used herein, the term "substantially no nimodipine related compound A" refers to an undetectable amount of nimodipine related compound A as measured by HPLC.

As used herein, the term "treat" or "treating" of a disease state includes: 1) inhibiting the disease state, i.e., arresting the development of the disease state or its clinical symptoms; 2) attenuating the disease state, i.e. reducing the number or intensity of one or more symptoms associated with the disease state, such that one or more symptoms is reduced but may, or may not be completely eliminated; and/or 3) relieving the disease state, i.e., causing temporary or permanent regression of the disease state or its clinical symptoms.

II. Compositions

In another embodiment, the present invention provides liquid compositions comprising nimodipine and a solvent system comprising water and one or more additional solvents. The amount of water in the solvent system from about 1% to about 25% (w/v), such as, for example, from about 1% to less than about 20%, from about 1% to about 15%, from about 1% to about 10%, from about 1% to 5%, from about 3% to less than about 20%, from about 3% to about 15%, from about 3% to about 10%, from about 3% to about 5%, from about 5% to less than about 20%, from about 5% to about 15%, from about 5% to about 10%, from about 7% to less than about 20%, from about 7% to about 15%, from about 7% to about 10%, from about 10% to less than about 20%, from about 10% to about 15%, or from about 15% to less than about 20%.

Exemplary solvents include, but are not limited to, water, glycerol, dimethylsulfoxide, N-methylpyrrolidone, dimethyl acetamide (DMA), dimethyl formamide, glycerol formal, ethoxy diglycol, triethylene glycol dimethyl ether, triacetin, diacetin, corn oil, acetyl triethyl citrate (ATC), ethyl lactate, polyglycolated capryl glycerides butyrolactone, dimethyl isosorbide, benzyl alcohol, ethanol, isopropyl alcohol, polyethylene glycol of various molecular weights, including but not limited to PEG 300 and PEG 400, or propylene glycol, or a mixture of one or more thereof.

In one embodiment, the liquid composition solvent system comprises PEG and at least one protic solvent selected from the group consisting of ethanol, glycerin, water, and combinations thereof. In such embodiments, PEG comprises at least about 50% (w/v) of the solvent system, such, as, for example, at least about 55%, at least about 60%, at least about 65%, at least about 70%, at least about 75%, at least about 80%, at least about 85% or at least about 90%. In other embodiments, PEG comprises from about 50% (w/v) to about 90% (w/v) of the solvent system, from about 50% (w/v) to about 80% (w/v) of the solvent system, from about 50% (w/v) to about 70% (w/v) of the solvent system, from about 50% (w/v) to about 60% (w/v) of the solvent system, from about 60% (w/v) to about 90% (w/v), from about 60% (w/v) to about 80% (w/v), from about 60% (w/v) to about 70% (w/v), from about 70% (w/v) to about 90% (w/v), from about 70% (w/v) to about 80% (w/v), or from about 80% (w/v) to about 90% (w/v). The remainder of the solvent system comprises the at least one protic solvent selected from the group consisting of ethanol, glycerin, water, and combinations thereof.

In one embodiment, the liquid composition comprises nimodipine and a solvent system comprising water and polyethylene glycol. The amount of water in the solvent system can vary from about 1% to about 35% (w/v), such as, for example, from about 1% to about 30%, from about 1% to about 25%, from about 1% to about 20%, from about 1% to about 15%, from about 1% to about 10%, from about 1% to about 5%, from about 5% to about 35%, from about 5% to about 30%, from about 5% to about 25%, from about 5% to about 20%, from about 5% to about 15%, from about 5% to about 10%, from about 10% to about 35%, from about 10% to about 30%, from about 10% to about 25%, from about 10% to about 20%, from about 10% to about 15%, from about 15% to about 35%, from about 15% to about 30%, from about 15% to about 25%, from about 15% to about 20%, from about 20% to about 35%, from about 20% to about 30%, from about 20% to about 25%, from about 25% to about 35%, from about 25% to about 30%, or from about 30% to about 35%. The amount of polyethylene glycol in the solvent system can vary from about 65% to about 99% (w/v), such as, for example, from about 65% to about 95%, from about 65% to about 90%, from about 65% to about 85%, from about 65% to about 80%, from about 65% to about 75%, from about 65% to about 70%, from about 70% to about 99%, from about 70% to about 95%, from about 70% to about 85%, from about 70% to about 80%, from about 70% to about 75%, from about 75% to about 99%, from about 75% to about 95%, from about 75% to about 90%, from about 75% to about 85%, from about 75% to about 80%, from about 80% to about 99%, from about 80% to about 95%, from about 80% to about 90%, from about 80% to about 85%, from about 85% to about 99%, from about 85% to about 95%, from about 85% to about 90%, from about 90% to about 99%, from about 90% to about 95% or from about 95% to about 99%. In a particular embodiment, the liquid composition comprises nimodipine and a solvent system consisting of water and polyethylene glycol.

In a particular embodiment, the liquid composition comprises nimodipine and a solvent system comprising from about 1% to about 35% (w/v) water and from about 65% to about 99% (w/v) polyethylene glycol. In another particular embodiment, the liquid composition comprises nimodipine and a solvent system comprising from about 1% to about 20% (w/v) water and from about 80% to about 99% (w/v) polyethylene glycol. In still another particular embodiment, the liquid composition comprises nimodipine and a solvent system from about 5% to about 20% (w/v) water and from about 80% to about 95% (w/v) polyethylene glycol.

In one embodiment, the liquid composition comprises nimodipine and a solvent system comprising water, polyethylene glycol, and ethanol. The amount of ethanol in the solvent system can vary from about 0.5% to about 5% (w/v), preferably from about 1% to less than about 5%, more preferably from about 0.5% to about 1%, as it has been found that higher amounts of ethanol lead to reduced nimodipine solubility (Example 2). The amount of water in the solvent system can vary from about 1% to about 35% (w/v), such as, for example, from about 1% to about 30%, from about 1% to about 25%, from about 1% to about 20%, from about 1% to about 15%, from about 1% to about 10%, from about 1% to about 5%, from about 5% to about 35%, from about 5% to about 30%, from about 5% to about 25%, from about 5% to about 20%, from about 5% to about 15%, from about 5% to about 10%, from about 10% to about 35%, from about 10% to about 30%, from about 10% to about 25%, from about 10% to about 20%, from about 10% to about 15%, from about 15% to about 35%, from about 15% to about 30%, from about 15% to about 25%, from about 15% to about 20%, from about 20% to about 35%, from about 20% to about 30%, from about 20% to about 25%, from about 25% to about 35%, from about 25% to about 30%, or from about 30% to about 35%. The amount of polyethylene glycol in the solvent system can vary from about 65% to about 97% (w/v), such as, for example, from about 65% to about 95%, from about 65% to about 95%, from about 65% to about 90%, from about 65% to about 80%, from about 65% to about 70%, from about 70% to about 97%, from about 70% to about 95%, from about 70% to about 90%, from about 70% to about 80%, from about 80% to about 97%, from about 80% to about 95%, from about 80% to about 90%, or from about 90% to about 97%, from about 90% to about 95%. In a particular embodiment, the liquid composition comprises nimodipine and a solvent system consisting of water, polyethylene glycol, and ethanol.

In a particular embodiment, the liquid composition comprises nimodipine and a solvent system comprising from about 0.5% to about 5% (w/v) ethanol, from about 1% to about 35% (w/v) water, and from about 65% to about 97% (w/v) polyethylene glycol. In another particular embodiment, the liquid composition comprises nimodipine and a solvent system comprising from about 0.5% to about 5% (w/v) ethanol, from about 1% to about 5% (w/v) water, and from about 50% to about 97% (w/v) polyethylene glycol. In still another particular embodiment, the liquid composition comprises nimodipine and a solvent system comprising from about 0.5% to about 1% (w/v) ethanol, from about 1% to about 5% (w/v) water, and from about 50% to about 97% polyethylene glycol.

In one embodiment, the liquid composition comprises nimodipine and a solvent system comprising water, polyethylene glycol, ethanol, and glycerin. The amount of ethanol in the solvent system can vary from about 0.4% to about 1% (w/v). The amount of water in the solvent system can vary from about 1% to about 25% (w/v), such as, for example, from about 1% to about 20%, from about 1% to about 15%, from about 1% to about 10%, from about 1% to about 5%, from about 5% to about 25%, from about 5% to about 20%, from about 5% to about 15%, from about 5% to about 10%, from about 10% to 25%, from about 10% to about 20%, from about 10% to about 15%, from about 15% to about 25%, from about 15% to about 20% or from about 20% to about 25%. The amount of polyethylene glycol in the solvent system can vary from about 50% to about 97% (w/v), such as, for example, from about 50% to about 95%, from about 50% to about 90%, from about 50% to about 80%, from about 50% to about 70%, from about 50% to about 60%, from about 60% to about 95%, from about 60% to about 95%, from about 60% to about 90%, from about 60% to about 80%, from about 60% to about 70%, from about 70% to about 97%, from about 70% to about 95%, from about 70% to about 90%, from about 70% to about 80%, from about 80% to about 97%, from about 80% to about 95%, from about 80% to about 90%, or from about 90% to about 97%, from about 90% to about 95%. The amount of glycerin in the solvent system can vary from about 1% to about 50% (w/v), such as, for example, from about 1% to about 40%, from about 1% to about 30%, from about 1% to about 20%, from about 1% to about 10%, from about 10% to about 50%, from about 10% to about 40%, from about 10% to about 30%, from about 10% to about 20%, from about 20% to about 50%, from about 20% to about 40%, from about 20% to about 30%, from about 30% to about 50%, from about 30% to about 40%, or from about 40% to about 50%. In a particular embodiment, the liquid composition comprises nimodipine and a solvent system consisting of water, polyethylene glycol, ethanol, and glycerin.

In a particular embodiment, the liquid composition comprises nimodipine and a solvent system comprising 0.4% to about 1% (w/v) ethanol, from about 1% to about 25% (w/v) water, from about 50% to about 97% (w/v) polyethylene glycol, and from about 1% to about 50% (w/v) glycerin. In another embodiment, the liquid composition comprises nimodipine and a solvent system comprising 0.4% to about 1% (w/v) ethanol, from about 1% to about 5% (w/v) water, from about 50% to about 97% (w/v) polyethylene glycol, and from about 1% to about 50% (w/v) glycerin. In still another particular embodiment, the liquid composition comprises nimodipine and a solvent system comprising about 0.4% to about 1% (w/v) ethanol, from about 1% to about 10% (w/v) water, from about 55% to about 75% (w/v) polyethylene glycol and from about 20% to about 40% (w/v) glycerin.

In one embodiment, the liquid composition consists essentially of nimodipine and one or more solvents listed above.

In other embodiments, the liquid composition comprises one or more additional excipients, such as, for example, buffering agents and/or preservatives.

Exemplary buffering agents include, but are not limited to, benzoic acid, phosphoric acid, tartaric acids, lactic acid, succinic acid, citric acid, acetic acid, ascorbic acid, aspartic acid, hydrochloric acid, sulfuric acid, glutamic acid, and salts thereof. In a particular embodiment, the buffering agent comprises sodium benzoate and benzoic acid.

In one embodiment, the preservative comprises from about 0.01% to about 0.1% (w/v) of the liquid composition.

The preservative can be from the paraben family. Exemplary paraben preservatives include, but are not limited to, methylparaben, propylparaben, ethylparaben, butylparaben, isobutylparaben, isopropylparaben, benzylparaben, sodium salts of the referenced parabens, or mixtures of thereof.

The preservative can be a sorbate (salt of sorbic acid and/or sorbic acid), benzoate (salt of benzoic acid and/or benzoic acid), sulfur dioxide, sulfite, nitrite, nitrate, lactic acid, propionic acid, propionate, ascorbic acid, ascorbate, butylated hydroxytoluene or combinations thereof. In one embodiment, the preservative comprises sodium benzoate and benzoic acid.

In one embodiment, the preservative comprises from about 0.01% to about 1% (w/v) of the liquid composition.

In still another embodiment, the liquid composition comprises an agent that functions as both a buffer and a preservative, e.g. sodium benzoate and benzoic acid.

The liquid composition comprises nimodipine in an effective amount per dosage unit. In one embodiment, the liquid composition comprises from about 10 mg to about 100 mg nimodipine per dosage unit, such as, for example, at least about 30 mg, at least about 40 mg, at least about 50 mg, at least about 60 mg or at least about 70 mg. In a particular embodiment, the liquid composition comprises about 60 mg or more nimodipine per dosage unit. In a more particular embodiment, the liquid composition comprises about 60 mg nimodipine per dosage unit.

The amount of solvent in the dosage unit can vary. In one embodiment, the liquid composition comprises from about 1 mL to about 20 mL solvent per dosage unit, such as, for example, from about 5 mL to about 20 mL, from about 5 mL to about 15 mL, from about 5 mL to about 10 mL, from about 10 mL to about 20 mL, from about 10 mL to about 15 mL or from about 15 mL to about 20 mL. In a particular embodiment, the liquid composition comprises about 5 mL of solvent per dosage unit. In another particular embodiment, the liquid composition comprises about 10 mL of solvent per dosage unit. In still another particular embodiment, the liquid composition comprises about 20 mL of solvent per dosage unit.

Accordingly, the concentration of nimodipine in the liquid composition of the present invention is greater than about 3 mg/mL, such as, for example, at least about 4 mg/mL, at least about 5 mg/mL, at least about 6 mg/mL, at least about 7 mg/mL, at least about 8 mg/mL, at least about 9 mg/mL, at least about 10 mg/mL, at least about 11 mg/mL, at least about 12 mg/mL, at least about 13 mg/mL, at least about 14 mg/mL, at least about 15 mg/mL, at least about 16 mg/mL, at least about 17 mg/mL, at least about 18 mg/mL, at least about 19 mg/mL or at least about 20 mg/mL.

In another embodiment, the concentration of nimodipine in the liquid composition is between any of the concentrations recited above, such as, for example, from about 5 mg/mL to about 20 mg/mL, from about 5 mg/mL to about 15 mg/mL, from about 5 mg/mL to about 10 mg/mL, about 10 mg/mL to about 20 mg/mL, from about 10 mg/mL to about 15 mg/mL and from about 15 mg/mL to about 20 mg/mL.

In a particular embodiment, the concentration of nimodipine in the liquid composition of the present invention is about 3 mg/mL to about 10 mg/mL, about 3 mg/mL to about 9 mg/mL, about 3 mg/mL to about 8 mg/mL, about 3 mg/mL to about 7 mg/mL, about 3 mg/mL to about 6 mg/mL, about 3 mg/mL to about 5 mg/mL, or about 3 mg/mL to about 4 mg/mL.

In another particular embodiment, the concentration of nimodipine in the liquid composition of the present invention is about 4 mg/mL to about 10 mg/mL, about 4 mg/mL to about 9 mg/mL, about 4 mg/mL to about 8 mg/mL, about 4 mg/mL to about 7 mg/mL, about 4 mg/mL to about 6 mg/mL or about 4 mg/mL to about 5 mg/mL.

In yet another particular embodiment, the concentration of nimodipine in the liquid composition of the present invention is about 5 mg/mL to about 10 mg/mL, about 5 mg/mL to about 9 mg/mL, about 5 mg/mL to about 8 mg/mL, about 5 mg/mL to about 7 mg/mL, or about 5 mg/mL to about 6 mg/mL.

In another particular embodiment, the concentration of nimodipine in the liquid composition of the present invention is about 6 mg/mL to about 10 mg/mL, about 6 mg/mL to about 9 mg/mL, about 6 mg/mL to about 8 mg/mL or about 6 mg/mL to about 7 mg/mL.

In one embodiment, the concentration of nimodipine in the liquid composition of the present invention is about 7 mg/mL to about 10 mg/mL, about 7 mg/mL to about 9 mg/mL or about 7 mg/mL to about 8 mg/mL.

In another embodiment, the concentration of nimodipine in the liquid composition of the present invention is about 8 mg/mL to about 10 mg/mL or about 8 mg/mL to about 9 mg/mL In still another embodiment, the concentration of nimodipine in the liquid composition is any of the concentrations recited above, such as, for example, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL or about 20 mg/mL.

In preferred embodiments, a dosage unit of the liquid composition comprises 60 mg nimodipine in about 5 mL solvents to about 10 mL of solvents, such as, for example, about 5 mL of solvent (12 mg/mL) or about 10 mL (6 mg/mL).

The density of the liquid composition may vary. In one embodiment, the density is between about 0.8 and about 1.8, such as, for example, between about 0.8 and about 1.0, about 1.0 and about 1.2, about 1.2 and about 1.4, about 1.4 and about 1.6, about 1.6 and about 1.8. In another embodiment, the density is about 0.8, about 0.9, about 1.0, about 1.1, about 1.2, 1.3, about 1.4, about 1.5, about 1.6, about 1.7 or about 1.0.

In a particular embodiment, the density is between 1.10 and about 1.26, more particularly, about 1.12 and about 1.24, about 1.14 and about 1.22, about 1.16 and about 1.20, and even more particularly, about 1.10, about 1.11, about 1.12, about 1.13, about 1.14, about 1.15, about 1.16, about 1.17, about 1.18, about 1.19, about 1.20, about 1.21, about 1.22, about 1.23, about 1.24, about 1.25 or about 1.26.

The liquid compositions of the present invention do not exhibit substantial nimodipine degradation when exposed to certain study conditions. Stability may be measured by any suitable method, e.g., by high-performance liquid chromatography (HPLC). In a particular embodiment, the liquid compositions of the present invention do not exhibit substantial nimodipine degradation under hydrolytic conditions, oxidative conditions, photolytic conditions, thermal conditions or combinations thereof. In another particular embodiment, the liquid compositions of the present invention do not exhibit substantial nimodipine degradation under forced stability conditions, accelerated stability conditions, real-time stability conditions or a combination thereof.

In some embodiments, the liquid compositions disclosed herein do not exhibit substantial degradation under accelerated conditions (e.g. 40° C. and 75% relative humidity) for at least 3 months, at least 6 months, at least 8 months, at least 10 months, at least 12 months, or at least 24 months. Methods of measuring nimodipine degradation are known to a person of skill in the art, e.g., monitoring the amount of nimodipine in the liquid composition by HPLC over a period of time. An exemplary method is provided in Example 1 infra.

In one embodiment, the liquid composition exhibits about 5% or less nimodipine degradation over at least a three-month period when exposed to 40° C. and 75% relative humidity, such as, for example, about 4.5% or less, 4.0% or less, about 3.5% or less, about 3.0% or less, about 2.5% or less, about 2.0% or less, about 1.5% or less or about 1.0% or less.

In a particular embodiment, the liquid composition exhibits about 1.0% or less nimodipine degradation over at least a three-month period when exposed to 40° C. and 75% relative humidity, such as, for example, about 0.90% or less, about 0.80% or less, about 0.70% or less, about 0.60% or less, about 0.50% or less, about 0.40% or less, about 0.30% or less, about 0.20% or less or about 0.10% or less.

In one embodiment, the liquid composition comprises a relatively smaller amount of nimodipine degradation compared with NYMALIZE® over at least a three month period when exposed to 40° C. and 75% relative humidity, i.e., less than about 5% degradation, from about 3% to about 4% degradation, from about 1% to about 2% degradation, from 0.01% to about 1% degradation, from about 0.01% to about 0.9% degradation, from about 0.01% to about 0.8% degradation, from about 0.01% to about 0.7% degradation, from about 0.01% to about 0.6% degradation, from about 0.01% to about 0.5% degradation, from about 0.01% to about 0.4% degradation, from about 0.01% to about 0.3% degradation, from about 0.01% to about 0.2% degradation, from about 0.01% to about 0.1% degradation and from about 0.01% to about 0.05% degradation.

In one embodiment, the liquid composition exhibits between about 0.50% and about 4.0%, about 0.50% and about 0.35%, about 0.5% and about 0.30%, about 0.50% and about 0.20%, about 0.50% and about 0.10%; about 0.10% and about 4.0%, about 1.0% and about 3.5%, about 1.0% and about 3.0%, about 1.0% and about 2.5%, about 1.0% and about 2.0%, about 1.5% and about 4.0%, about 1.5% and about 3.5%, about 1.5% and about 3.0%, about 1.5% and about 2.5%, about 1.5% and about 2.0%, about 2.0% and about 2.5 nimodipine degradation over at least a three month period when exposed to 40° C. and 75% relative humidity In a particular embodiment, the liquid composition exhibits about 95% or less, about 90% or less, about 85% or less, about 80% or less, about 76% or less, about 70% or less, about 65% or less, 60% or less, about 55% or less, about 50% or less, about 45% or less, about 40% or less, about 35% or less, about 30% or less, about 25% or less, about 20% or less, about 15% or less, about 10% or less nimodipine degradation than NYMALIZE® over at least a three month period when exposed to 40° C. and 75% relative humidity.

In another particular embodiment, the liquid composition exhibits about 1.0% to about 90%, about 1.0% and about 80%, about 1.0% and about 70%, about 1.0% and about 60%, about 1.0% and about 50%, about 1.0% to about 40%, about 1.0% to about 30%, about 1.0% to about 20%, about 1.0% to about 10% or less nimodipine degradation than NYMALIZE® over at least a three-month period when exposed to 40° C. and 75% relative humidity.

In another particular embodiment, the liquid composition exhibits about 10% to about 90%, about 10% and about 80%, about 10% and about 70%, about 10% and about 60%, about 10% and about 50%, about 10% to about 40%, about 10% to about 30%, or about 10% to about 20% less nimodipine degradation than NYMALIZE® over at least a three-month period when exposed to 40° C. and 75% relative humidity.

In another particular embodiment, the liquid composition exhibits about 20% to about 90%, about 20% and about 80%, about 20% and about 70%, about 20% and about 60%, about 20% and about 50%, about 20% to about 40%, or about 20% to about 30% less nimodipine degradation than NYMALIZE® over at least a three-month period when exposed to 40° C. and 75% relative humidity.

In yet another particular embodiment, the liquid composition exhibits about 40 to about 70% or about 50 to about 60% less nimodipine degradation than NYMALIZE® over at least a three month period when exposed to 40° C. and 75% relative humidity.

One particular nimodipine degradation product that can be minimized using the liquid compositions of the present invention is nimodipine related compound A. In certain embodiments, the liquid composition comprises from 0.01% to about 1.5% nimodipine related compound A over at least a three-month period when exposed to 40° C. and 75% relative humidity, such as, for example, from about 0.01% to about 0.1% and from about 0.01% to about 0.05%.

In a particular embodiment, the liquid composition comprises about 1.9% or less nimodipine related compound A over at least a three month period when exposed to 40° C. and 75% relative humidity, or more particularly, about 1.8% or less, about 1.7% or less, about 1.6% or less, about 1.5% or less, about 1.4% or less, about 1.3 or less, or about 1.2% or less. In a particular embodiment, the liquid composition comprises about 1.9% or less nimodipine related compound A over at least six-month period when exposed to 40° C. and 75% relative humidity In a particular embodiment, the liquid composition comprises about 1.2% or less nimodipine related compound A over at least a three month period when exposed to 40° C. and 75% relative humidity, or more particularly, about 1.0% or less, about 0.90% or less, about 0.80% or less, about 0.70% or less, about 0.60% or less, about 0.50% or less, about 0.40% or less, about 0.30% or less, about 0.20% or less, about 0.10% or less about 0.08% or less, about 0.06% or less, about 0.04% or less, about 0.02% or less, or about 0.01% or less nimodipine related compound A.

In one embodiment, the liquid composition comprises from 0.01% to about 1.2% nimodipine related compound A over at least a three month period when exposed to 40° C. and 75% relative humidity, and more particularly, about 0.01% to about 1.0%, about 0.01% to about 0.20%, about 0.01% to about 0.40%, about 0.01 to about 0.60%, about 0.01% to about 0.80%, about 0.01% to about 1.0%, about 0.01% to about 1.2% nimodipine related compound A.

In one embodiment, the liquid composition comprises from 0.1% to about 1.2% nimodipine related compound A over at least a three-month period when exposed to 40° C. and 75% relative humidity, and more particularly, about 0.1% to about 1.0%, about 0.1% to about 0. 20%, about 0.1% to about 0.40%, about 0.1 to about 0.60%, about 0.1% to about 0.80%, about 0.1% to about 1.0%, about 0.1% to about 1.2% nimodipine related compound A.

In a particular embodiment, the liquid composition contains substantially no nimodipine related compound A over at least a three-month period when exposed to 40° C. and 75% relative humidity In one embodiment, the liquid composition contains about 100% or less, 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, or about 10% or less nimodipine related compound A than NYMALIZE® over at least a three month period when exposed to 40° C. and 75% relative humidity.

In a particular embodiment, the liquid composition contains between about 1.0% and about 90% less, about 1.0% and about 80% less, about 1.0% and 70%, about 1.0% and about 60%, about 1.0% and about 50%, about 1.0% and about 30%, about 1.0% and about 20%, about 1.0% and about 10%, about 1.0% and about 5.0% less nimodipine related compound A than NYMALIZE® over at least a three-month period when exposed to 40° C. and 75% relative humidity, In a particular embodiment, the liquid composition contains between about 10% and about 90% less, about 10% and about 80% less, about 10% and 70%, about 10% and about 60%, about 10% and about 50%, about 10% and about 30%, about 10% and about 20%, about 20% and about 90%, about 20% and about 80%, about 20% and about 70%, about 20% and about 60%, about 20% and about 50%, about 20% and about 40%, about 20% and about 30%, about 30% and about 90%, about 30% and about 80%, about 30% and about 70%, about 30% and about 60%, about 30% and about 50%, or about 30% and about 40% less nimodipine related compound A than NYMALIZE® over at least a three month period when exposed to 40° C. and 75% relative humidity.

In one embodiment, the liquid composition of the present invention comprises less than about 3.0% total impurities over at least a three-month period when exposed to 40° C. and 75% relative humidity such as, for example, about 2.9% or less, about 2.8% or less, about 2.6% or less, about 2.4% or less, about 2.2% or less, or about 2.0% or less total impurities.

In one embodiment, the liquid composition of the present invention comprises less than about 2.0% total impurities over at least a three-month period when exposed to 40° C. and 75% relative humidity such as, for example, about 1.9% or less, about 1.8% or less, about 1.6% or less, about 1.4% or less, about 1.2% or less, about 1.0% or less, about 0.8% or less or about 0.6%, about 0.4% or less or about 0.2% or less total impurities.

In a particular embodiment, the liquid composition of the present invention comprises between about 0.1% and about 2.0% total impurities over at least a three month period when exposed to 40° C. and 75% relative humidity, or more particularly, about 0.1% and about 1.8%, about 0.1% and about 1.6% total impurities, about 0.1% and about 1.4%, about 0.1% and about 1.2%, about 0.1% and 1.0%, about 0.1% and about 0.8%, about 0.1% and about 0.6%, about 0.1% and about 0.4%, or about 0.1% and about 0.2% total impurities.

In one embodiment, the liquid composition contains about 100% or less, 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, or about 10% or less total impurities than NYMALIZE® over at least a three month period when exposed to 40° C. and 75% relative humidity.

In one embodiment, the liquid composition comprises about 1.0% and about 90% less, about 1.0% and about 80% less, about 1.0% and 70%, about 1.0% and about 60%, about 1.0% and about 50%, about 1.0% and about 30%, about 1.0% and about 20%, about 1.0% and about 10%, or about 1.0% and about 5.0% less total impurities than NYMALIZE® over at least a three-month period when exposed to 40° C. and 75% relative humidity.

In one embodiment, the liquid composition comprises about 10% and about 90% less, about 10% and about 80% less, about 10% and 70%, about 10% and about 60%, about 10% and about 50%, about 10% and about 30%, about 10% and about 20% less total impurities than NYMALIZE® over at least a three-month period when exposed to 40° C. and 75% relative humidity.

In one embodiment, the liquid composition comprises about 20% and about 90% less, about 20% and about 80% less, about 20% and 70%, about 20% and about 60%, about 20% and about 50%, or bout 20% and about 30% less total impurities than NYMALIZE® over at least a three-month period when exposed to 40° C. and 75% relative humidity.

In one embodiment, the liquid composition comprises about between about 40 and about 70% or about 50 and about 60% less total impurities than NYMALIZE® over at least a three-month period when exposed to 40° C. and 75% relative humidity.

In one embodiment, the liquid compositions of the present invention comprise substantially no impurities over at least a three month period when exposed to 40° C. and 75% relative humidity.

In some embodiments, the liquid compositions disclosed herein do not exhibit substantial degradation under ambient conditions (e.g. 25° C. and 60% relative humidity) for at least 3 months, at least 6 months, at least 8 months, at least 10 months, at least 12 months, or at least 24 months. In a particular embodiment, the liquid compositions disclosed herein do not exhibit substantial degradation under ambient conditions (e.g. 25° C. and 60% relative humidity) about 24 months or greater, such as, e.g., 26 months, 28 months, 30 months or more.

In a particular embodiment, the liquid compositions disclosed herein do not exhibit 10% or more nimodipine degradation over at least a three month period when exposed to 25° C. and 60% relative humidity and more particularly, about 9% or more, about 8% or more, about 7% or more, about 6% or more, about 5% or more, about 4% or more, about 3% or more, about 2% or more, about 1% or more. In a particular embodiment, the liquid compositions disclosed herein do not exhibit about 1.0% or more nimodipine degradation over at least a three-month period when exposed to 25° C. and 60% relative humidity and more particularly, about 0.9% or more, about 0.8% or more, about 0.7% or more, about 0.6% or more about 0.5% or more, about 0.4% or more, about 0.3% or more, about 0.2% or more, about 0.1% or more or about 0.01% or more.

One particular nimodipine degradation product that can be minimized using the liquid compositions of the present invention is nimodipine related compound A.

In one embodiment, the liquid composition comprises 1.2% or less nimodipine related compound A over at least a three-month period when exposed to 25° C. and 60% relative humidity, or more particularly, about 1.2% or less, about 1.1% or less, about 1.0% or less, about 0.9% or less or about 0.8% or less nimodipine related compound A.

In one embodiment, the liquid composition comprises 0.6% or less nimodipine related compound A over at least a three-month period when exposed to 25° C. and 60% relative humidity.

In one embodiment, the liquid composition comprises 0.5% or less nimodipine related compound A over at least a three-month period when exposed to 25° C. and 60% relative humidity, and more particularly, 0.4% or less, 0.35% or less, 0.30% or less, 0.25% or less, 0.20% or less, 0.15% or less, 0.10% or less or 0.05% or less nimodipine related compound A.

In certain embodiments, the liquid composition comprises from 0.01% to about 0.35% nimodipine related compound A over at least a three month period when exposed to 25° C. and 60% relative humidity, such as, for example, from about 0.01% to about 0.30%, about 0.01% to about 0.25%, about 0.01% to about 0.20%, about 0.01% to about 0.15%, about 0.01% to about 0.10%; about 0.1% to about 0.35%, about 0.10% to about 0.30%, about 0.10% to about 0.25%, about 0.10% to about 0.20% or about 0.10% to about 0.15% nimodipine related compound A.

In a particular embodiment, the liquid composition contains about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less or about 10% or less nimodipine related compound A than NYMALIZE® over at least a three month period when exposed to 25° C. and 60% relative humidity, In another particular embodiment, the liquid composition contains between about 50% and about 100% less, between about 50% and about 95% less, between about 50% and about 85% less, between about 50% and about 80% less, between about 50% and about 75% or between about 50% and about 70% or less nimodipine related compound A than NYMALIZE® over at least a three-month period when exposed to 25° C. and 60% relative humidity.

In one embodiment, the liquid composition contains substantially no nimodipine related compound A over at least a three-month period when exposed to 25° C. and 60% relative humidity.

In one embodiment, the total impurities in liquid compositions of the present invention comprises less than about 1.8% over at least a three-month period when exposed to 25° C. and 60% relative humidity, such as, for example, about 1.6% or less, about 1.4% or less, about 1.2%, about 1.0% or less, about 0.8% or less, about 0.6% or less, about 0.4% or less, about 0.2% or less, about 0.1% or less or 0.0% or less total impurities.

In one embodiment, the total impurities in liquid compositions of the present invention comprises less than about 0.7% over at least a three-month period when exposed to 25° C. and 60% relative humidity, such as, for example, about 0.5% or less or about 0.3% or less, and more particularly, less than about 0.6%, less than about 0.5%, less than about 0.4%, less than about 0.3%, less than about 0.2%, less than about 0.1%, less than about 0.05% or less than about 0.01% total impurities.

In one embodiment, the liquid compositions of the present invention comprise about 100% or less total impurities than NYMALIZE® over at least a three month period when exposed to 25° C. and 60% relative humidity, In one embodiment, the liquid composition of the present invention comprises about 95% or less total impurities than NYMALIZE® over at least a three month period when exposed to 25° C. and 60% relative humidity, such as, e.g., about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less about 5% or less total impurities.

In one embodiment, the liquid composition of the present invention comprises substantially no total impurities over at least a three-month period when exposed to 25° C. and 60% relative humidity.

In one embodiment, the liquid composition is packaged as a single dosage unit. In an alternate embodiment, the liquid composition is packaged in a container containing multiple dosage units, e.g., a bottle. In still another embodiment, the liquid composition is packaged into a pre-filled syringe. The liquid composition can be dispensed, for example, by loading into an automated medication dispensing system, by extraction with an oral dosing device, such as a cup or syringe, or by pouring the composition directly into a device (e.g., a syringe or machine) for administration to a patient. Other means for providing, preparing, storing, transporting, and dispensing pharmaceutical compositions are known to those skilled in the art.

In one embodiment, the shelf life of the liquid composition is increased relative to compared with NYMALIZE®. The shelf-life of a drug is generally defined as the length of time a drug can stay on the shelf without degrading to unacceptable levels of chemical potency or pharmaceutical utility. Shelf-life may be determined by any suitable method.

In a particular embodiment, the shelf life of the liquid composition is increased by about 5%, about 10%, about 15%, about 20%, about 25%, about 30%, about 35%, about 40%, about 45%, about 50% or more.

In another particular embodiment, the shelf life of the liquid composition is increased by about one week, about two weeks, about three weeks, about four weeks, up to one month, up to 2 months, up to 3 months, up to 4 months, up to 5 months, up to 6 months or more than 6 months.

In one embodiment, the shelf life of the liquid when it is contained in a suitable container exhibits a shelf life of at least 6 months, more preferably at least 12 months, still more preferably at least 15 months, yet more preferably at least 18 months, most preferably at least 21 months and in particular at least 24 months. In one embodiment, the shelf-life is greater than 24 months, e.g., 26 months, 28 months, 30 months or more.

In one embodiment, the shelf life of the liquid composition when it is contained in a suitable container container exhibits a shelf life under ambient conditions of at least 6 months, more preferably at least 12 months, still more preferably at least 15 months, yet more preferably at least 18 months, most preferably at least 21 months and in particular at least 24 months. In one embodiment, the shelf-life is greater than 24 months, e.g., 26 months, 28 months, 30 months or more.

III. Methods

The present invention provides a method of treating a disorder, or symptoms associated with a disorder, for which nimodipine provides a therapeutic effect. Nimodipine acts as a vasodilator and is considered to be a calcium channel blocker and was approved by the FDA to improve neurological outcome after subarachnoid hemorrhage (SAH) from ruptured blood vessels in the brain.

Accordingly, the present invention provides a method of improving neurological outcome by reducing the incidence and severity of ischemic deficits in patients with subarachnoid hemorrhage from ruptured intracranial berry aneurysms comprising administering to a patient in need thereof an effective amount of a liquid composition comprising nimodipine described supra.

The liquid composition is preferably administered enterally. Suitable enteral administration routes include, but are not limited to, oral, via nasogastric tube or via gastric tube. In a particular embodiment, the liquid composition is administered to the patient via nasogastric tube.

A dosage unit of the liquid composition is first administered after the subarachnoid hemorrhage, such as, for example, within about 100 hours of the subarachnoid hemorrhage, within about 90 hours of the subarachnoid hemorrhage, within about 80 hours of the subarachnoid hemorrhage, within about 70 hours of the subarachnoid hemorrhage, within about 60 hours of the subarachnoid hemorrhage, within about 50 hours of the subarachnoid hemorrhage, within about 40 hours of the subarachnoid hemorrhage, within about 30 hours of the subarachnoid hemorrhage, within about 20 hours of the subarachnoid hemorrhage, within about 10 hours of the subarachnoid hemorrhage or within about 5 hours of the subarachnoid hemorrhage. In a particular embodiment, a dosage unit of the liquid composition is administered within about 96 hours of the subarachnoid hemorrhage.

A dosage unit of the liquid composition can be administered to the patient once a day or multiple times a day, such as, for example, twice or more per day, three times or more per day, four times or more per day, five times or more per day or six times or more per day.

A dosage unit of the liquid composition can be administered in various intervals, such as, for example, every two hours, every four hours, every six hours, every eight hours, every 12 hours or every 24 hours. In a particular embodiment, a dosage unit of the liquid composition is administered to the patient every four hours.

The duration of treatment can vary. In one embodiment, treatment is continued for at least 7 days, at least 14 days, at least 21 days or at least 30 days. In a particular embodiment, the dosing regimen is continued for 21 days.

In exemplary embodiments, a dosage unit of the liquid composition is administered every four hours for 21 days. The first dosage unit is administered within 96 hours of the subarachnoid hemorrhage. The dosage unit preferably comprises 60 mg nimodipine.

The liquid composition can be dosed before or after feeding. In one embodiment, a dosage unit is administered about 1 hour prior to a meal. In another embodiment, a dosage unit is administered about two hours after a meal.

The present invention also provides a method of treating other conditions including, but not limited to, vasospastic angina, Prenzmetal's angina, stable angina, acute myocardial infarction, myocardial arrest, arrhythmia, systemic hypertension, pulmonary hypertension, congestive heart failure, and hypertrophic cardiomyopathy comprising administering to a patient in need thereof an effective amount of a liquid composition comprising nimodipine described supra.

In a particular embodiment, the method of the present invention is associated with decreased instances of diarrhea compared to NYMALIZE®, i.e., about 100%, about 90%, about 80%, about 70%, about 60%, about 50%, about 40%, about 30%, about 20%, about 10% decrease in instance measured over the period of a day, week or month.

EXAMPLES

Example 1: Stability Study

Two non-aqueous liquid compositions of the present invention were compared to NYMALIZE® over the course of a 3-month accelerated stability study. The non-aqueous liquid compositions were prepared with the following ingredients:

A. Formulation A (2017NIM009)

A 10 liter batch was prepared with the ingredients shown in Table 1, below. The pH of the batch was adjusted to within pH 6 to 7 with 6N HCl and 6N NaOH after completion.

TABLE I

Formula A (2017NIM009)

| Material | % W/V | Theoretical Amount (g) | Actual Amount (g) |
|---|---|---|---|
| Nimodipine | 0.60 | 60.00 | 60.06 |
| PEG 400 | 68.00 | 6,800.00 | 6,806.64 |
| Ethanol 95% | 0.395 | 39.50 | 39.51 |
| Glycerin | 47.505 | 4,750.50 | 4,757.62 |
| Total | 116.5 | 11,650.00 | 11,663.83 |

B. Formulation B (2017nim010)

A 10 liter batch was prepared with the ingredients shown in Table II, below.

TABLE II

Formula B (2017NIM010)

| Material | % w/v | Theoretical Amount (g) | Actual Amount (g) |
|---|---|---|---|
| Nimodipine | 0.60 | 60.00 | 60.00 |
| PEG 400 | 68.00 | 6,800.00 | 6,800.54 |
| Ethanol 95% | 0.395 | 39.50 | 39.52 |
| Glycerin | 47.505 | 4,745.25 | 4,750.09 |
| Benzoic Acid | 0.0375 | 3.75 | 3.75 |
| Sodium Benzoate | 0.015 | 1.50 | 1.50 |
| Total | 116.5 | 11,650.00 | 11,655.40 |

C. Formulation C (2017NIM013)

A 5 liter batch was prepared with the ingredients shown in Table III, below:

TABLE III

Formulation C (2017NIM013)

| Material | % w/v | Theoretical Amount (g) | Actual Amount (g) |
|---|---|---|---|
| Nimodipine | 0.60 | 30.00 | 30.00 |
| PEG 400 | 68.00 | 3400.00 | 3410.00 |
| Ethanol 95% | 0.395 | 19.975 | 19.78 |
| Glycerin | 47.505 | 2375.25 | 2374.33 |
| Methylparaben | 0.20 | 10.00 | 10.00 |
| Total | 116.7 | 5835.00 (5000 mL) | 5844.11 |

Samples of all three compositions were stored at 40° C. and 75% relative humidity (RH). The amount of nimodipine present in the same was measured at one month, two month and three-month time points by HPLC. Formation of degradants ("related substances") and nimodipine related compound A (NRCA) were also measured by HPLC at the same time points. The results of the study are shown in Table IV, below:

TABLE IV

Amount of Nimodipine/Formation of Degradants Over Time for NYMALIZE ® and Formulations A, B and C stored at 40° C. and 75% RH

| Test | Time Period/ Storage Condition | NYMALIZE ® | Formulation A (2017nim009) | Formulation B (2017nim010) | Formulation C (2017nim013) |
|---|---|---|---|---|---|
| Assay (% LC) | Initial | 100.1 | 101.7 | 102.4 | 103.9 |
| | 1 month 40/75 | 98.5 | 103.4 | 102.9 | 101.1 |
| | 2 month 40/75 | 97.5 | 100.2 | 100.5 | 100.1 |
| | 3 month 40/75 | 96.0 | 100.1 | 99.4 | 101.5 |
| | 6 month 40/75 | 92.1 | 100.1 | 97.8 | 99.9 |
| Total Impurities | Initial | ND | ND | 0.1 | ND |
| | 1 month 40/75 | 0.80 | 0.21 | 0.51 | 0.10 |
| | 2 month 40/75 | 1.40 | 0.45 | 0.69 | 0.13 |
| | 3 month 40/75 | 2.10 | 0.99 | 0.77 | 0.40 |
| | 6 month 40/75 | 3.0 | 1.5 | 1.9 | ND |
| Compound A | Initial | ND | ND | 0.1 | ND |
| | 1 month 40/75 | 0.8 | 0.2 | 0.5 | 0.1 |
| | 2 month 40/75 | 1.4 | 0.5 | 0.7 | 0.1 |
| | 3 month 40/75 | 2.1 | 1.0 | 0.8 | 0.4 |
| | 6 month 40/75 | 3.0 | 1.5 | 1.9 | ND |

ND = not detected

Samples of all three compositions were stored at 25° C. and 60% relative humidity (RH). The amount of nimodipine present in the same was measured at one month, two month and three month time points by HPLC. Formation of degradants ("related substances") and nimodipine related compound A (NRCA) were also measured by HPLC at the same time points. The results of the study are shown below:

TABLE V

Amount of Nimodipine/Formation of Degradants Over Time for NYMALIZE ® and Formulations A, B and C stored at 25° C. and 60% RH

| Test | Time Period/ Storage Condition | NYMALIZE ® | Formulation A (2017nim009) | Formulation B (2017nim010) | Formulation C (2017nim013) |
|---|---|---|---|---|---|
| Assay (% LC) | Initial | 100.1 | 101.7 | 102.4 | 103.9 |
|  | 1 month 25/60 | — | — | — | — |
|  | 2 month 25/60 | — | — | — | 101.6 |
|  | 3 month 25/60 | 100.3 | 100.6 | 101.6 | 100.6 |
|  | 6 month 25/60 | 99.7 | 101.3 | 101.7 |  |
| Total Impurities | Initial | 0.0 | ND | 0.1 | ND |
|  | 1 month 25/60 | — | — | — | ND |
|  | 2 month 25/60 | — | — | — | ND |
|  | 3 month 25/60 | 0.5 | ND | ND | ND |
|  | 6 month 25/60 | 0.7 | 0.3 | 0.2 |  |
| Compound A | Initial | ND | ND | ND | ND |
|  | 1 month 25/60 | — | — | — | — |
|  | 2 month 25/60 | — | — | — | ND |
|  | 3 month 25/60 | 0.4 | ND | ND | ND |
|  | 6 month 25/60 | 0.6 | 0.1 | 0.1 | ND |

Blank = ND

HPLC methodology for detection of nimodipine and for detection of nimodipine related substances is as follows.
Detection of Nimodipine An Inertsil ODS-2 150×4.6 mm HPLC column, 5 μm (example part number 5020-01124) or equivalent column is used with a C8 or C18 pre-column (example part number Phenomenex AJO-4287 or equivalent). Reagents and solutions include deionized water (CAS #7732-18-5), HPLC grade methanol (CAS #67-56-1), tetrahydrofuran (THF, CAS #109-99-9) and nimodipine reference standard (CAS #66085-59-4). A 1000 mL mobile phase solution consists of 600 mL water, 200 mL methanol and 200 mL tetrahydrofuran. Degas for 10 minutes.
Chromatographic Conditions
Column: Inertsil ODS-2 150×4.6 mm HPLC column, 5 example part number 5020-01124 (GL Sciences) or equivalent
Guard Column: C8 or C18 (example Phenomenex, Cat. No. AJ0-4287) or equivalent
Temperature: 40° C. (Column)
Flow Rate: 1.8 mL/minute
Detection: Photodiode Array (PDA) detector
Injection Volume: 10 μL
Run Time: Approximately 45 minutes for Standard injections and approximately 85 minutes for Sample injections.
Pump: Isocratic
Elution Time: If methylparaben is present in the formulation, the retention time (RT) is approximately 3 min. The retention time of Nimodipine Related Compound A is approximately 15-19 minutes. The retention time of nimodipine is approximately 21-26 minutes.

Use a suitable HPLC system that provides comparable resolution, reproducibility, and sensitivity. Due to differences in columns and instrumentation, it may be necessary to adjust the mobile phase composition and/or instrument parameters to achieve system suitability requirements. Chromatographic parameters are not adversely affected by small HPLC parameter changes that could potentially be encountered in the average laboratory environment or small variations in the performance associated with HPLC equipment from different vendors.

The mobile phase contains a high concentration of tetrahydrofuran, which can lower the burst strength of some plastic materials. It is recommended that the HPLC lines to and post column are composed of stainless steel or other resistant materials.

To prepare the working standard solution, accurately weigh approximately 60 mg of Nimodipine Reference Standard into a 50 mL actinic volumetric flask. Add 10 mL THF and sonicate 10 minutes to dissolve. Bring to volume with mobile phase: Mix well.

Accurately weigh approximately 20 mL of sample solution into a low actinic 50 mL volumetric flask. Add 10 mL of THF and shake mechanistically (for example, wrist-action shaker) for 5 minutes. Dilute to volume with mobile phase. Store at 4° C. (2-8° C.). Concentration is approximately 1.2 mg/mL nimodipine.

Due to differences in columns and instrumentation, it may be necessary to adjust the mobile phase composition and/or instrument parameters to achieve system suitability requirements. Chromatographic parameters are not adversely affected by small HPLC parameter changes that could potentially be encountered in the average laboratory environment or small variations in the performance associated with HPLC equipment from different vendors. Please note that the nimodipine HPLC run needs sufficient time to equilibrate. It is recommended that multiple working standard injections be performed for equilibration prior to analysis. Inject the Nimodipine Working Standard Solution. Inject a blank solution of mobile phase to prevent possible carry-over. Inject the Nirnodipine Sample Preparation. The absorption spectrum of the preparation of the test specimen containing nimodipine exhibits maxima only at the same wavelengths as that of a similar preparation of the corresponding Nimodipine Reference Standard. As the solvents included as part of the sample preparation can contribute to noise at the lower wavelengths, it is recommended that the spectrum comparison be performed between 220-400 nm.

Detection of Nimodipine Related Substances

An Inertsil ODS-2 150×4.6 mm HPLC column, 5 μm (example part number 5020-01124) or equivalent column is used with a C8 or C18 pre-column (example part number Phenomenex AJO-4287 or equivalent). Reagents and solutions include deionized water (CAS #7732-18-5), HPLC grade methanol (CAS #67-56-1), tetrahydrofuran (THF, CAS #109-99-9), 3% hydrogen peroxide and nimodipine reference standard (CAS #66085-59-4). A 1000 mL mobile phase solution will consist of 600 mL water, 200 mL methanol and 200 mL tetrahydrofuran. Degas for 10 minutes.

Chromatographic Conditions

Column: Inertsil ODS-2 150×4.6 mm HPLC column, 5 μm, example part number 5020-01124 (GL Sciences) or equivalent Guard Column: C8 or C18 (example Phenomenex, Cat. No. AJ0-4287) or equivalent Temperature: 40° C. (Column)

Flow Rate: 1.8 mL/minute

Detection: UV absorbance at 271 nm.

Injection Volume: 10 μL

Run Time: Approximately 45 minutes for Standard injections and approximately 85 minutes for Sample injections.

Pump: Isocratic

Elution Time: If methylparaben is present in the formulation, the retention time (RT) is approximately 3 min. The retention time of Nimodipine Related Compound A is approximately 15-19 minutes. The retention time of nimodipine is approximately 21-26 minutes.

Use a suitable HPLC system that provides comparable resolution, reproducibility, and sensitivity. Due to differences in columns and instrumentation, it may be necessary to adjust the mobile phase composition and/or instrument parameters to achieve system suitability requirements. Chromatographic parameters are not adversely affected by small HPLC parameter changes that could potentially be encountered in the average laboratory environment or small variations in the performance associated with HPLC equipment from different vendors.

Please note that the mobile phase contains a high concentration of tetrahydrofuran, which can lower the burst strength of some plastic materials. It is recommended that the HPLC lines to and post column are composed of stainless steel or other resistant materials.

To prepare the standard solution, accurately weigh approximately 10 mg (+/−1 mg) of nimodipine Related Compound A Reference Standard into a 50 mL actinic volumetric flask. Add 5 mL THF and sonicate 10 minutes to dissolve. Bring to volume with mobile phase. Dilute to volume with mobile phase. Mix well. Store at 4° C. (Concentration is approximately 0.2 mg/mL Related A). Transfer 3.0 mL of the above stock solution into a 100 mL volumetric flask. Dilute to volume with mobile phase (Concentration is approximately 0.006 mg/ml Related A, or 0.5% of the analytical sample concentration of Nimodipine Related Compound A). Prepare the above Nimodipine Related Compound A Reference Standard in duplicate. The first preparation will be considered the Nimodipine Related Compound A Working Standard Solution, and the second preparation will be considered the Nimodipine Related Compound A Check Standard Solution.

To prepare the resolution standard solution, accurately weigh approximately 60 mg of Nimodipine Reference Standard into a 50 mL actinic volumetric flask. Add 10 mL THF and sonicate 10 minutes to dissolve. Bring to volume with mobile phase: Mix well. Pipette 5.0 mL of the above solution into a glass tube or other appropriate heat-resistant container. Add 0.5 mL of the 3% hydrogen peroxide and heat at 90° C. in the oven for 1 hour. Allow to cool to room temperature. Transfer quantitatively into a low actinic 10 mL volumetric flask. Dilute to volume with mobile phase. Mix well. Store at 4° C. Discard when analyses are complete.

After injecting the Resolution Standard, inject the mobile phase twelve times for greater than or equal to one minute each. For the Waters HPLC systems, diluent may be injected eleven times for 4 minutes each, and once for 10 minutes prior to injecting standards. The extended run time (extended from a run time of one minute per mobile phase injection) is to allow for equilibration of the baseline after elution of the solvent front and may be altered on a system to system basis. Please note that the intent of this preparation is not for quantitation, but to confirm resolution between nimodipine and the peak immediately prior to nimodipine, at RRT 0.9 (wherein RRT stands for Relative Retention Time)

Accurately weigh approximately 20 mL of sample solution into a low actinic 50 mL volumetric flask. Add 10 mL of THF and shake mechanistically (for example, wrist-action shaker) for 5 minutes. Dilute to volume with mobile phase. Store at 4° C. Concentration is approximately 1.2 mg/mL nimodipine.

Inject the Nimodipine Resolution Standard. For the Nimodipine Resolution Standard, Resolution (R) between the unknown peak before nimodipine (RRT 0.9) and nimodipine in the resolution solution should be not less that (NLT) 1.0 (R>=1.0). Inject the diluent solution as prescribed above post injection of the Resolution Standard.

Inject the Nimodipine Related Compound A Working Standard six times. The percent relative standard deviation (%RSD) should be less than or equal to 10%. Please note that equilibration injections of the standard may be allowed post the injections of the Nimodipine Resolution standard and diluent injections.

Inject the Nimodipine Related Compound A Check Standard Solution two times. Comparison of the average peak area responses (area per unit weight) (n=2) of the check standard and working standard (n=6) is ±10%.

Inject in duplicate each sample preparation and inject a standard in duplicate after every six samples. Quantify the known related compounds and any additional peaks of unknown individual impurities.

Example 2: Solubility Studies

The solubility of nimodipine in various aqueous solvent systems was evaluated. Samples were prepared with the solvent systems shown in Tables VI-IX. The individual solvents were prepared first, and then nimodipine was added incrementally and mixed using a magnetic stirrer and stir bar for at least 30 minutes at room temperature, until visual saturation was achieved. The individual solutions were centrifuged, filtered, prepared into analytical diluent, and then injected onto the HPLC system to confirm the actual nimodipine concentration in each solution.

TABLE VI

Nimodipine solubility in glycerin, ethanol, water, and PEG400 when PEG400 is held constant

| Glycerin % | Ethanol % | Water % | PEG400% | Nimodipine mg/mL |
|---|---|---|---|---|
| 55 | 0.4 | 1 | 43 | 5.2 |
| 51 | 0.4 | 5 | 43 | 4.3 |
| 46 | 0.4 | 10 | 43 | 1.5 |
| 36 | 0.4 | 20 | 43 | 1.5 |

TABLE VII

Nimodipine solubility in glycerin, ethanol, water, and PEG400 when glycerin is held constant

| Glycerin % | Ethanol % | Water % | PEG400% | Nimodipine mg/mL |
|---|---|---|---|---|
| 35 | 0.4 | 1 | 63 | 13.4 |
| 35 | 0.4 | 5 | 59 | 10.0 |
| 35 | 0.4 | 10 | 54 | 5.7 |
| 36 | 0.4 | 20 | 43 | 1.5 |

TABLE VIII

Nimodipine solubility in ethanol, water, and PEG400

| Glycerin % | Ethanol % | Water % | PEG400% | Nimodipine mg/mL |
|---|---|---|---|---|
| 0 | 1.0 | 10 | 89 | 31 |
| 0 | 5.0 | 10 | 85 | 29 |
| 0 | 1.0 | 20 | 79 | 18 |
| 0 | 5.0 | 20 | 75 | 14 |

TABLE IX

Nimodipine solubility in water and PEG400

| Glycerin % | Ethanol % | Water % | PEG400% | Nimodipine mg/mL |
|---|---|---|---|---|
| 0 | 0 | 1 | 99 | 43 |
| 0 | 0 | 5 | 95 | 38 |

TABLE IX-continued

Nimodipine solubility in water and PEG400

| Glycerin % | Ethanol % | Water % | PEG400% | Nimodipine mg/mL |
|---|---|---|---|---|
| 0 | 0 | 10 | 90 | 26 |
| 0 | 0 | 15 | 85 | 14 |
| 0 | 0 | 25 | 75 | 10 |
| 0 | 0 | 40 | 60 | 1.3 |
| 0 | 0 | 50 | 50 | 0.4 |

TABLE X

Nimodipine solubility in glycerin, water, and PEG400 when PEG400 is held constant at 60%

| Glycerin % | Ethanol % | Water % | PEG400% | Nimodipine mg/mL |
|---|---|---|---|---|
| 39 | 0 | 1 | 60 | 2.1 |
| 30 | 0 | 10 | 60 | 1.6 |
| 20 | 0 | 20 | 60 | 1.5 |

The invention claimed is:

1. A liquid composition comprising nimodipine and a solvent system that comprises from about 50% to about 97% (w/v) PEG, about 1 to about 10% (w/v) water, from about 0.4% to about 1% (w/v) ethanol, and from about 1% to about 50% (w/v) glycerin, wherein the concentration of nimodipine is about 6 mg/mL or about 12 mg/ml, and wherein about 5% or less nimodipine degradation is observed over a period of at least six months when exposed to 40° C. and 75% relative humidity.

2. The liquid composition of claim 1, wherein the solvent system consists of PEG, water, ethanol, and glycerin.

3. The liquid composition of claim 1, wherein the solvent system comprises from about 65% to about 97% (w/v) PEG, from about 5% to about 35% (w/v) water, and from about 0.5% to about 5% (w/v) ethanol.

4. The liquid composition of claim 3, wherein the solvent system comprises from about 0.5% to about 1% (w/v) ethanol.

5. The liquid composition of claim 1, wherein nimodipine is present in an amount of about 60 mg per dosage unit.

* * * * *

UNITED STATES PATENT AND TRADEMARK OFFICE
CERTIFICATE OF CORRECTION

| | |
|---|---|
| PATENT NO. | : 11,517,563 B2 |
| APPLICATION NO. | : 17/708669 |
| DATED | : December 6, 2022 |
| INVENTOR(S) | : Hugh Greg Thomas |

It is certified that error appears in the above-identified patent and that said Letters Patent is hereby corrected as shown below:

In the Claims

Column 26, Claim 3, cancel the text "from about 5% to about 35% (w/v) water, and from about 0.5% to about 5% (w/v) ethanol."

Signed and Sealed this
Twenty-first Day of March, 2023

Katherine Kelly Vidal
*Director of the United States Patent and Trademark Office*